US011124475B2

(12) United States Patent
Zheng et al.

(10) Patent No.: US 11,124,475 B2
(45) Date of Patent: Sep. 21, 2021

(54) HYDROGEN SULFIDE DONOR IN ORGANIC SALT FORM AND PREPARATION METHOD THEREFOR

(71) Applicant: CHENGDU KAOENSI SCIENCE AND TECHNOLOGY CO., LTD., Sichuan (CN)

(72) Inventors: Hu Zheng, Sichuan (CN); Lingling Weng, Sichuan (CN)

(73) Assignee: CHENGDU KAOENSI SCIENCE AND TECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 16/625,840

(22) PCT Filed: Mar. 15, 2018

(86) PCT No.: PCT/CN2018/079115
§ 371 (c)(1),
(2) Date: Mar. 13, 2020

(87) PCT Pub. No.: WO2018/233326
PCT Pub. Date: Dec. 27, 2018

(65) Prior Publication Data
US 2020/0199067 A1   Jun. 25, 2020

(30) Foreign Application Priority Data

Jun. 21, 2017   (CN) .......................... 201710475428.5

(51) Int. Cl.
| | | |
|---|---|---|
| *C07C 277/08* | (2006.01) | |
| *C07C 279/14* | (2006.01) | |
| *C07C 279/18* | (2006.01) | |
| *C07C 279/26* | (2006.01) | |
| *C07C 279/28* | (2006.01) | |
| *C07D 209/16* | (2006.01) | |
| *C07D 213/73* | (2006.01) | |
| *C07D 233/50* | (2006.01) | |
| *C07D 233/64* | (2006.01) | |
| *C07D 245/02* | (2006.01) | |
| *C07D 277/48* | (2006.01) | |
| *C07D 295/027* | (2006.01) | |
| *C07D 295/215* | (2006.01) | |
| *C07D 487/04* | (2006.01) | |

(52) U.S. Cl.
CPC .......... *C07C 277/08* (2013.01); *C07C 279/14* (2013.01); *C07C 279/18* (2013.01); *C07C 279/26* (2013.01); *C07C 279/28* (2013.01); *C07D 209/16* (2013.01); *C07D 213/73* (2013.01); *C07D 233/50* (2013.01); *C07D 233/64* (2013.01); *C07D 245/02* (2013.01); *C07D 277/48* (2013.01); *C07D 295/027* (2013.01); *C07D 295/215* (2013.01); *C07D 487/04* (2013.01)

(58) Field of Classification Search
None
See application file for complete search history.

(56) References Cited

U.S. PATENT DOCUMENTS

| 4,017,539 A * | 4/1977 | Bosies ................. C07C 279/26 |
| | | 564/233 |
| 2006/0041145 A1* | 2/2006 | Hayashi ............... C07D 213/32 |
| | | 546/339 |
| 2020/0299251 A1* | 9/2020 | Zou .................... B01D 53/1493 |

FOREIGN PATENT DOCUMENTS

| CN | 102078327 A | 6/2011 |
| CN | 102503932 A | 6/2012 |
| CN | 108929250 A * | 12/2018 |

OTHER PUBLICATIONS

CAS Abstract and Indexed Compound, M. Trisha et al., European Journal of Organic Chemistry, 7334-7343 (2015) (Year: 2015).*
M. Trisha et al., European Journal of Organic Chemistry, 7334-7343 (2015) (Year: 2015).*
J. Wang et al., 272 International Journal of Pharmaceutics, 129-135 (2004) (Year: 2004).*
M. Achterhof et al., 53 Journal of the American Chemical Society, 2682-2688 (1931) (Year: 1931).*
CAS Abstract and Indexed Compounds M. Achterhof et al., 53 Journal of the American Chemical Society, 2682-2688 (1931) (Year: 1931).*
CAS Abstract CAS Registry No. RN 1173600-12-8 (2009) (Year: 2009).*
A. Koning et al., 46 Nitric Oxide, 37-49 (2015) (Year: 2015).*
B. Wilinski et al., 65 Pharmaceutical Reports, 737-742 (2013) (Year: 2013).*
J. Beltowsk, 67 Pharmaceutical Reports, 647-658 (2015) (Year: 2015).*
Y. Markus, 48 J. Chem. Thermodynamics, 70-74 (2012) (Year: 2012).*
R. Zhao et al., 145 Analyst, 2305-2310 (2020) (Year: 2020).*
Moore et al., "Chemistry Biochemistry and Pharmacology of Hydrogen Sulfide", Handbook of experimental pharmacology, vol. 230, Springer International Publishing, Switzerland 2015.

(Continued)

*Primary Examiner* — Alexander R Pagano
(74) *Attorney, Agent, or Firm* — Novick, Kim & Lee, PLLC; Allen Xue

(57) ABSTRACT

A hydrogen sulfide donor in an organic salt form and a preparation method thereof. The hydrogen sulfide donor exists as a salt formed by organic compounds with an alkaline motif and hydrogen sulfide with weak acidity. The hydrogen sulfide donor features with a simple structure, and an easy preparation method. Moreover, hydrogen sulfide donors in different forms can be prepared according to research and development needs. After the hydrogen sulfide donor enters an organism, the process of in vivo dissociation and hydrogen sulfide supply is simple, rapid, and effective, and there is no requirement for enzyme or any other complicated condition, and thus, the hydrogen sulfide donor has a great application prospect and value.

7 Claims, 1 Drawing Sheet

(56) References Cited

OTHER PUBLICATIONS

Sun et al., "Taurine Supplementation Lowers Blood Pressure and Improves Vascular Function in Prehypertension Randomized, Double-Blind, Placebo-Controlled Study", Hypertension, 2016,vol. 67, Issue 3; 541-549.

Zhao et al., "Design, Synthesis and Cardioprotective Effect of N-Mercapto-Based Hydrogen Sulfide Donors", Journal of Medicinal Chemistry, 2015, 58(18):7501-7511.

Wang et al., "Advances in Hydrogen Sulphide and Hydrogen Sulphide-Releasing Drugs", Acta Pharmaceutica Sinica 51(4), Apr. 12, 2016, pp. 507-516.

Tang et al., "Synthesis, Characterization and Reaction with H2S of Poly(allylamine)", Advanced Engineering Sciences; vol. 49(3), May 20, 2017, pp. 197-201.

Luo et al., "Research Progress in Biological Functions of Hydrogen Sulphide Donors"; Medical Science Journal of Central South China; vol. 44, No. 1, Jan. 15, 2016, pp. 107-111.

\* cited by examiner

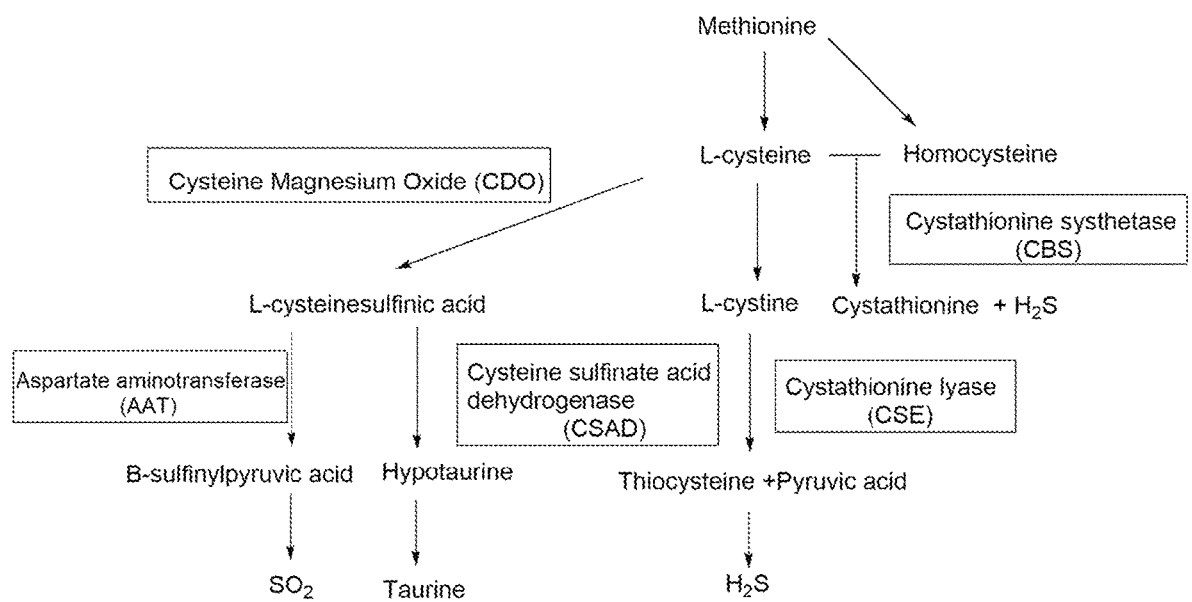

HYDROGEN SULFIDE DONOR IN ORGANIC SALT FORM AND PREPARATION METHOD THEREFOR

TECHNICAL FIELD

The present invention relates to one new form of hydrogen sulfide donor that may have research and/or medicinal values.

BACKGROUND ART

It is well known that hydrogen sulfide ($H_2S$) is considered not to have any medical use due to its foul smell, high toxicity, and being poisonous gas. But nearly more than 10 years, based on the understanding of its effects on the physiological and pathological processes in in vivo biological system, it is surprisingly found that endogenous $H_2S$ has wide biological effects and great medicinal potency.

For hydrogen sulfide, its molecular weight is 34, boiling point is −63.33° C., and this gas is 1.13 times heavier than air. At room temperature, it is gas, and if there are 0.02~0.13 ppm $H_2S$ in air, its odor can be smelt. 0.5 g $H_2S$ can dissolve in 100 mLl water at the temperature of 10° C., while only 0.3 g $H_2S$ can dissolve in 100 ml water at the temperature of 20° C., whose pH value is 4.5. $H_2S$ can form a stable salt with alkali metals such as Na, K, Ca, alkaline earth metals or $NH_3$.

Since $H_2S$ is found to be an endogenous molecular gas in organisms, it causes a wide interest as much the same as NO and CO, and becomes the hot spot and frontier topics in the world scientific research field. The research field mainly includes the in vivo formation mechanism of $H_2S$, the in vivo molecular biology research of $H_2S$ such as the molecular regulatory mechanisms for cells and the relevance of $H_2S$ to major diseases and its molecular mechanism, as well as the investigation on hydrogen sulfide donor to develop its medical values.

The investigation indicates that $H_2S$ in body can at least be naturally produced by using sulfur-containing amino acids such as L-cysteine as substrates under the action of three enzymes such as cystathionine γ-lyase (CSE), cystathionine β-synthase (CBS), and 3-mercaptopyruvate sulfurtransferase (3-MST), etc, and can also be produced by spontaneous red blood cell response to glucose and sulfur as well as reduced glutathione (GSH). The in vivo metabolic process of sulfur amino acid is shown in FIG. 1.

For research on the in vivo biological regulation of $H_2S$, special attention is currently paid to its relationship with asthma, atherosclerosis and diabetes, hypertension and other diseases. Recently, the relationship of $H_2S$ and oncology also draws a lot of attention, and the main target point is the expression of $H_2S$-related enzyme or gene levels.

As the report (Qiangian Sun et al., Hypertension, 2016, 67(3), 541-9), excessive salt intake in human body can lead to the development of hypertention. Thus, the World Health Organization (WHO) suggests the daily salt intake for healthy people should be less than 6 g. The investigation shows that if $H_2S$ donor such as taurine is introduced into the body, exogenous $H_2S$ can be produced in body, that can thus be used as the endogenous defense system of hypertension resulted from the salt, because it is found that during the process of the hypertension, the level of $H_2S$ in people with prehypertention is obviously reduced.

The investigation has suggested that the use of inorganic $H_2S$ donors including $Na_2S$, $(NH_4)_2S$ and so on all has showed meaningful results in the research on animal brain ischemia such as blood flow, hemorheology, etc. (Yu Zhao et al, Design, Synthesis and Cardioprotective Effect of N-Mercapto-Based Hydrogen Sulfide Donors, J. Med. Chem. (2015, 58(18): 7501-7511)).

For the donors of hydrogen sulfide, three kinds have recently been reported, including inorganic $H_2S$ donors such as $Na_2S$, NaHS, CaS; organic $H_2S$ donors such as sulfur-containing organic compounds; organic synthetic $H_2S$ donors such as aspirin analogue, ibuprofen hybrid analogue, etc. The research on their chemical structures, pharmacological activities, and molecular biology including the biological regulation on cells, the effects on enzymes and gene expression has become more and more extensive and deeper (Philip K. Moore, Chemistry Biochemistry and Pharmacology of Hydrogen Sulfide, Springer International Publishing, Switzerland 2015).

Content of the Invention

Based on above-mentioned, the present invention will provide one new structural type of hydrogen sulfide ($H_2S$) donor, i.e. the hydrogen sulfide donor in organic salt form, that may have research and/or medicinal developmental values, and further provide the corresponding preparative method thereof.

The hydrogen sulfide donor in organic salt form according to the present invention is a salt structure yielded by organic compounds with basic moiety and hydrogen sulfide ($H_2S$). Since hydrogen sulfide is an acidic component, the organic compound molecules capable of forming salts with $H_2S$ need have corresponding basic moiety, and the stronger the alkaline, the more stable the formed salt. In general, the donors in salt structural form that are produced by organic compounds with basic moiety and hydrogen sulfide all have enough stability, if the pH value of said organic compounds in 1 mol/L solution is ≥9.5.

It is well known that for said organic compounds with basic moiety, most of them are those containing nitrogen or nitrogenated groups in the molecular structures, including open chain, monocyclic or polycyclic aliphatic compounds and compounds having an aromatic ring and/or heterocyclic structure and so on (in each structure, R and $R_1$-$R_4$ can respectively be $C_{1-3}$ alkane or alkene; X can respectively be the groups containing O, S, N; n=1-2). For example, said compounds include but not limited to those listed in the following.

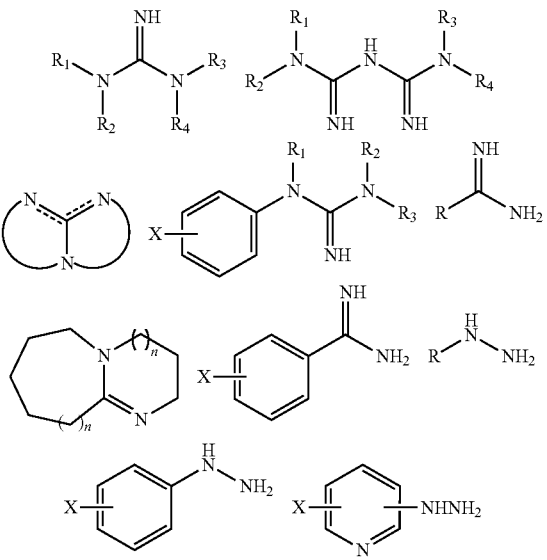

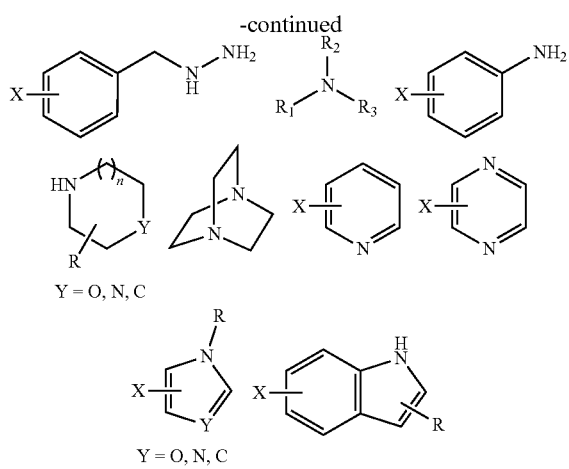

Because the hydrogen sulfide donor of the present invention is a salt structural substance yielded by organic compounds with basic moiety and hydrogen sulfide, it can have a dissolution process in body fluids of organisms or humans, same with those of inorganic hydrogen sulfide donors such as sodium sulfide, sodium hydrosulfide, etc., that can make hydrogen sulfide easily and quickly liberate and release, and don't need like other reported forms of organic hydrogen sulfide donors. It is necessary for said organic donors to liberate hydrogen sulfide even through complicated in vivo physiological/biochemical reactions with the aid of different enzymes.

Among above organic compounds having basic moiety that can form salts with hydrogen sulfide, as far as the interference or effect on the physiological processes of organisms (especially human bodies) is said, compounds can include those producing effects on related physiological functions and/or pharmacological activities in organisms, as well as those not producing any physiological functions and/or pharmacological activities and not having adverse consequences yet. Thus, the latter compounds can also be said "neutral compounds" acceptable by organisms. After the latter "neutral compounds" form the salt structural donors with hydrogen sulfide and then the donors enter the organism and dissociate, the donors can only produce the active moiety hydrogen sulfide. Thus, although this kind of hydrogen sulfide donor can not be excluded the use in the development of drug, its greater application advantages lie in the research on related physiological/pharmacological actions of hydrogen sulfide under the conditions of precluding the effect of other factors. According to the research and understanding on related physiological/pharmacological actions of hydrogen sulfide, the hydrogen sulfide donor is chosen that is formed by salification with said basic organic compounds having corresponding physiological/pharmacological activities for organisms, especially humans, to realize the purpose and effect that their beneficial actions can combine or complement each other and/or their respective unbeneficial actions can restrict or counteract each other. That can not only be used in the research on the actions of hydrogen sulfide, but also can be directly used in the drug development.

In particular, above-mentioned basic organic compounds containing nitrogen or nitrogenated groups can include those having guanidines, amidines, hydrazines etc, for example, said basic organic compounds containing nitrogen or nitrogenated groups can include but not limited to those basic amino acid compounds such as arginine, lysine, etc.

In addition, said basic organic compounds containing nitrogen or nitrogenated groups can further include reported and/or used alkaloids having or not having physiological/pharmacological activities.

For various kinds of basic organic compounds that can be used in hydrogen sulfide donors, at present, preferable compounds may be shown by experiments as basic groups of compounds in the form of therapeutic drugs for the current diseases closely related with hydrogen sulfide. Said drugs include but not limited to metformin or similar excellent drugs for treatment of diabetes. These drugs are prepared as the salts of hydrogen sulfide, and becomes the drug-hydrogen sulfide donor compounds, that is thus good for the formation of dual-acting targets or synergy.

As hydrogen sulfide is an acid gas having certain solubility in water, and said basic structural compounds capable of forming salts with hydrogen sulfide also have certain solubility in water, the general preparative method for hydrogen sulfide donor in organic salt form according to the present invention includes that the raw materials are dissolved in water or other good solvents, and then hydrogen sulfide gas is added to form salts. The reaction mixture is subjected to usual workup ways such as precipitation, filtration, concentration or recrystallization, etc., and after separation from the solvent, the target compound can be obtained as solid. These are well-known conventional salification reactions, as well as the preparative methods and processes of salt compounds in the art. For example, the hydrogen sulfide salts of base compounds in the form of drugs such as arginine, guanethidine, clonidine, moroxydine, phenformine, cimetidine and so on can be prepared by above method. Additionally, using this method, the alkaloids such as berberine, fibrauretin, etc., can be prepared as hydrogen sulfide salts. For current undruggable bases such as hydrazine compounds, after being prepared as hydrogen sulfide salts, the salts can further be used in deeply exploring, studying and understanding the properties of hydrogen sulfide salts.

For some base compounds such as free alkali with poor stablility, the common or commercially available forms are mostly stable salt compounds such as hydrochlorate, sulfate, carbonate, etc. Thus, another alternative convenient way for the preparation of hydrogen sulfide salt is that based on different salt forms, the free base can be obtained by treatment with alkaline reagents including sodium hydroxide, barium hydroxide, silver ammonia and so on; or by treatment under conditions of strong alkaline including sodium ethoxide, sodium methoxide and so on; or by treatment with strong or weak basic ion exchange resin. Then, hydrogen sulfide or its water solution or ethanol solution is added to the mixture, to convert the base compounds into hydrogen sulfide salts. The reaction temperature is generally in the range of $-10 \sim 50°$ C. After completion of reaction, the product hydrogen sulfide can be obtained by filtration or low-temperature vacuum drying and other methods.

In the following, the above content of the present invention is further illustrated by referring to the specific examples, as shown in the FIGURE, but it should not be construed that the above subject scope of the present invention is only limited to the following examples. Without departing from above technical spirit of the present invention, various alternations or changes, made according to the common technical knowledge and conventional means in the art, are all included in the scope of the present invention.

DESCRIPTION OF FIGURE

FIG. 1 is the schematic diagram showing the in vivo metabolic process of sulfur amino acids reported in literature.

EXAMPLES

Example 1 Preparation of Guanidine Free Base (1)

At room temperature, to a 1000 mL round-bottom long-neck flask with the dry tube of anhydrous calcium chloride (or other suitable drying agents), was added absolute ethanol (500 mL), then the cut metal sodium (2.53 g, 110 mmol) was added in portions, and sodium ethoxide solution was obtained after complete dissolution of sodium. Metformin hydrochloride (18.10 g, 110 mmol) was added to the solution of sodium ethoxide in portions, and then lots of white solid suspended in the solution. After finishing the addition, the mixture was heated to 60° C. and allowed to react for 1 h, and then cooled to room temperature and filtered, to obtain the white solid (6.0 g). After dried in phosphorus pentoxide dryer, the crude product (13.88 g) was obtained as white solid. The crude product (5 g) was dissolved in acetone under sonication for desalting, and the filtrate was concentrated to dry, to obtain guanidine free base as white solid. m.p. 108-110° C.

$^1$H NMR (400 MHz, $D_2O$): δ 2.87 (s, 6H);
$^{13}$C NMR (100 MHz, $D_2O$): δ 37.14 (2C), 158.44, 161.55.
The structure is:

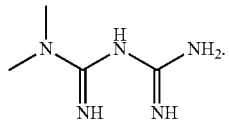

Example 2 Preparation of Guanidine Free Base (2)

At room temperature, metformin hydrochloride (1.65 g, 10 mmol) was dissolved in 10 mL water, to which was added aq. odium hydroxide solution (5 mL, 2 mol/L), and the mixture was stirred at room temperature for 1 h. The water was removed by concentration under reduced pressure, to obtain the white solid, that was desalted using acetone to provide metformin free base with strong alkaline as white solid. M.p. of crude product was 90-100° C., and after recrystallization, m.p. of the product was 110-112° C.

Example 3 Preparation of Guanidine Free Base (3)

At 50° C., to the suspension of metformin hydrochloride (16.6 g, 100 mmol) in isopropanol (70 mL), was added potassium hydroxide (5.88 g, 105 mmol) under stirring, and the mixture was kept at 50° C. and allowed to react for 2 h, then cooled to room temperature and filtered. The filter cake was washed with isopropanol and acetone, and the washing solution and the filtrate were combined and concentrated. The resultant solid was desalted using acetone to provide metformin free base with strong alkaline as white solid. M.p. of crude product was 90-100° C., and after recrystallization, m.p. of the product was 110-112° C.

Example 4 Preparation of Guanidine Free Base (4)

At room temperature, silver oxide (460 mg, 2 mmol) was suspended in 8 ml distilled water under vigorously stirring, to which was drop added 10 times diluted concentrated ammonia (9.5 mL). After the reaction solution was clear, to the freshly prepared solution of silver ammonia ([Ag(NH$_3$)$_2$]$^+$OH$^-$), was added metformin hydrochloride (660 mg, 4 mmol), and lots of white precipitation appeared. At room temperature, the mixture was stirred for additional 30 min and filtered, and the filtrate was concentrated to dry under reduced pressure, to provide the product.

Example 5 Preparation of Guanidine Free Base (5)

At room temperature, guanidine sulfate (1.21 g, 10 mmol) was dissolved in 10 mL distilled water, to which was added freshly prepared aqueous solution of barium hydroxide (5 mL, 2 mol/L). After stirring at room temperature for 30 min, water was evaporated under reduced pressure to obtain the pale yellow oil, that was placed at room temperature overnight and became solid, to provide the target compound.

$^{13}$C NMR (100 MHz, $D_2O$): δ 160.98, 162.45.

Example 6 1,1-dimethylbiguanide hydrogen sulfide salt ($C_4H_{11}N_5 \cdot H_2S$, MW: 163.24)

1,1-Dimethylbiguanide (26 g, 0.2 mol) in one of examples 1-4 was taken and mixed with 100 mL water, and under the conditions that the temperature was kept at 2° C., 100 ml aqueous solution of 6.8 g hydrogen sulfide was added and mixed. The mixed solution was freeze-dried for 24 h, to provide the white solid that was collected to obtain the target compound.

$^1$H NMR (400 MHz, $D_2O$): δ 3.01 (s, 6H);
$^{13}$C NMR (100 MHz, $D_2O$): δ 37.45 (2C), 158.39, 160.15.
Elemental analysis: for $C_4H_{15}N_5OS$; Cacld: C, 29.43%, H, 8.03%, N, 42.90%, S, 19.64%;
Found: C, 28.16%, H, 8.36%, N, 41.39%, S, 17.46%.
The water content in sample was 11.58%.
The content of reducing substance was 88.2% by iodometric titration. The structure is:

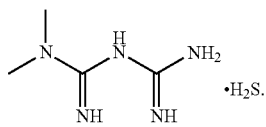

Example 7 L-Arginine Hydrogen Sulfide Salt ($C_6H_{14}N_4O_2 \cdot H_2S$, MW: 208.28)

L-arginine monohydrate (38.4 g, 0.2 mol) was mixed with 100 mL water, and under the conditions that the temperature was kept at 25° C., hydrogen sulfide was added 0.5 h. Then, the mixed solution was freeze-dried for 24 h, to provide the white solid, that was collected to obtain the product.

$^1$H NMR (400 MHz, $D_2O$): δ 1.54-1.74 (m, 4H), 3.17 (t, J=6.7 Hz, 2H), 3.43 (t, J=6.0 Hz, 1H);
$^{13}$C NMR (100 MHz, $D_2O$): δ 24.44, 31.58, 40.73, 54.94, 156.70, 179.27.

The water content in sample was 12.9%.
The content of reducing substance was 69.2% by iodometric titration. The structure is:

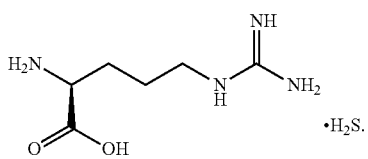

Example 8 Morpholine Biguanide Hydrogen Sulfide Salt (C₆H₁₃N₅O.H₂S, MW: 205.28)

Morpholine biguanide (34.2 g, 0.2 mol) was mixed with 100 mL water, and under the conditions that the temperature was kept at 25° C., hydrogen sulfide was added 0.5 h. Then, the mixed solution was rotary evaporated at 50° C. to remove water and provide the white solid (46 g), that was collected to obtain the target compound.

$^1$H NMR (400 MHz, D$_2$O): δ 3.35 (t, J=4.0 Hz, 1H), 3.46 (t, J=4.0 Hz, 2H), 3.67 (t, J=4.0 Hz, 1H), 3.71 (t, J=4.0 Hz, 2H);

$^{13}$C NMR (100 MHz, D$_2$O): δ 45.08, 65.99, 158.86, 160.33;

Elemental analysis: for C$_6$H$_{15}$N$_5$OS, Cacld: C, 35.11%, H, 7.37%, N, 34.12%, S, 15.62%;

Found: C, 29.31%, H, 8.36%, N, 27.29%, S, 12.46%.

The water content in sample was 16.26%.

The content of reducing substance was 76.3% by iodometric titration. The structure is:

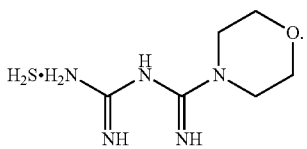

Example 9 P-Guanidinobenzoic Acid Hydrogen Sulfide Salt (C₈H₉N₃O₂.H₂S, MW: 213.26)

P-guanidinobenzoic acid (35.8 g, 0.2 mol) was mixed with 100 mL absolute ethanol, and under the conditions that the temperature was kept at 10° C., hydrogen sulfide was added 1 h. Then, the mixed solution was rotary evaporated at 45° C. to remove the solvent and provide the white solid (41 g), that was collected to obtain the target compound.

Elemental analysis: for C$_8$H$_{11}$N$_3$O$_2$S, Cacld: C, 45.06%, H, 5.20%, N, 19.70%, S, 15.04%;

Found: C, 38.99%, H, 5.56%, N, 17.29%, S, 13.03%.

The water content in sample was 3.72%.

The content of reducing substance was 85.5% by iodometric titration. The structure is:

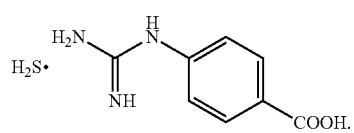 [SMILES: N=C(N)Nc1ccc(C(=O)O)cc1]

Example 10 Cyanoguanidine Hydrogen Sulfide Salt (C₂H₄N₄.H₂S, MW: 118.16)

Cyanoguanidine (16.8 g, 0.2 mol) was mixed with 100 mL absolute ethanol, and under the conditions that the temperature was kept at 2° C., 100 mL ethanol solution of 6.8 g hydrogen sulfide was added 1 h. Then, the mixed solution was rotary evaporated at 45° C. to remove the solvent and provide the white solid (23 g), that was collected to obtain the target compound.

Elemental analysis: for C$_2$H$_6$N$_4$S, Cacld: C, 20.33%, H, 5.12%, N, 47.42%, S, 27.14%;

Found: C, 16.59%, H, 5.59%, N, 38.68%, S, 22.14%.

The water content in sample was 5.36%.

The content of reducing substance was 86.2% by iodometric titration. The structure is:

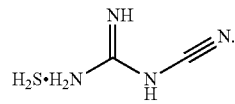

Example 11 Guanidine Acetate Hydrogen Sulfide Salt (C₃H₇N₃O₂.H₂S, MW: 151.19)

Guanidine acetate (23.4 g, 0.2 mol) was mixed with 100 mL dichloromethane, and at room temperature, the solution was drop added to a three-necked bottle filled with hydrogen sulfide. The mixture was stirred 3 h at room temperature, and white solid precipitated, that was filtered and dried in vacuum, to provide the white solid (26 g), that was collected to obtain the target compound.

Elemental analysis: for C$_3$H$_9$N$_3$O$_2$S, Cacld: C, 23.83%, H, 6.00%, N, 27.79%, S, 21.21%;

Found: C, 20.68%, H, 6.43%, N, 24.26%, S, 18.41%.

The water content in sample was 3.58%.

The content of reducing substance was 90.2% by iodometric titration. The structure is:

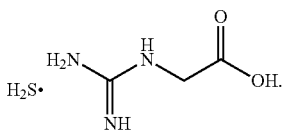

Example 12 Famotidine Hydrogen Sulfide Salt (C₈H₅N₇O₂S₃.H₂S, MW: 371.53)

Famotidine (6.74 g, 0.02 mol) was mixed with 100 mL tetrahydrofuran, and under the conditions that the temperature was kept at 30° C., hydrogen sulfide was added 2 h. Then, the mixed solution was rotary evaporated at 40° C. to remove the solvent and provide the white solid (7.3 g), that was collected to obtain the target compound.

Elemental analysis: for C$_8$H$_{17}$N$_7$O$_2$S$_4$, Cacld: C, 25.86%, H, 4.61%, N, 26.39%, S, 34.52%;

Found: C, 23.18%, H, 5.03%, N, 23.58%, S, 30.85%.

The water content in sample was 4.62%.

The content of reducing substance was 93.7% by iodometric titration. The structure is:

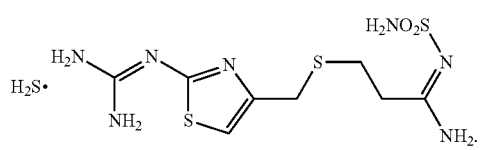

Example 13 Guanethidine Hydrogen Sulfide Salt (C₉H₂₁N₅·H₂S, MW: 233.38)

Guanethidine (4.00 g, 0.02 mol) was mixed with 100 mL tetrahydrofuran, and at room temperature, the solution was drop added to a reaction bottle filled with hydrogen sulfide. The mixture was allowed to react 12 h at room temperature, and solid was produced after freeze-drying at 0-5° C., then filtered and provided the white solid (3.6 g), that was collected to obtain the target compound.

Elemental analysis: for C₉H₂₃N₅S, Cacld: C, 46.32%, H, 9.93%, N, 30.01%, S, 13.74%;

Found: C, 41.31%, H, 10.93%, N, 26.69%, S, 12.22%.

The water content in sample was 3.93%.

The content of reducing substance was 92.6% by iodometric titration. The structure is:

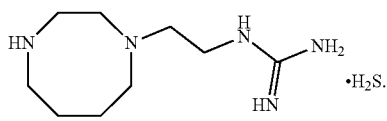

Example 14 Clonidine Hydrogen Sulfide Salt (C₉H₉C₁₂N₃·H₂S, MW: 264.17)

Clonidine (4.58 g, 0.02 mol) was mixed with 50 mL dichloromethane, to which was added 50 ml ethanol solution of 3.9 g hydrogen sulfide at 0° C. Under the conditions that the temperature was kept at 0° C., the mixture was allowed to react 2 h, and then solid was produced after freeze-drying at 0-5° C., filtered and provided the white solid (3.6 g), that was collected to obtain the target compound.

Elemental analysis: for C₉H₁₁Cl₂N₃S, Cacld: C, 40.92%, H, 4.20%, Cl, 26.84%, N, 15.91%, S, 12.14%;

Found: C, 37.16%, H, 4.33%, Cl, 24.34%, N, 14.65%, S, 11.02%.

The water content in sample was 2.72%.

The content of reducing substance was 93.3% by iodometric titration. The structure is:

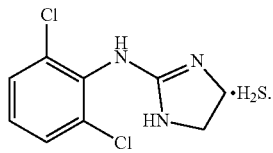

Example 15 Cimetidine Hydrogen Sulfide Salt (C₁₀H₁₆N₆S·H₂S, MW: 286.42)

Cimetidine (5.04 g, 0.02 mol) was mixed with 50 mL ethyl acetate, to which was added 50 ml ethyl acetate solution of 3.9 g hydrogen sulfide at 0° C. Under the conditions that the temperature was kept at 0° C., the mixture was allowed to react 3 h, and then solid was produced after freeze-drying at 0-5° C., filtered and provided the white solid (2.9 g), that was collected to obtain the target compound.

Elemental analysis: for C₁₀H₁₈N₆S₂, Cacld: C, 41.93%, H, 6.33%, N, 29.34%, S, 22.39%;

Found: C, 36.11%, H, 6.76%, N, 25.51%, S, 19.26%.

The water content in sample was 6.52%.

The content of reducing substance was 91.9% by iodometric titration. The structure is:

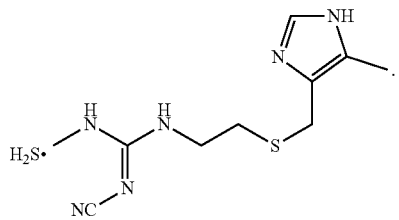

Example 16 Guanoclor Hydrogen Sulfide Salt (C₉H₁₂Cl₂N₄O·H₂S, MW: 297.20)

Guanoclor (5.25 g, 0.02 mol) was mixed with 100 mL dichloromethane, and under the conditions that the temperature was kept at 0° C., hydrogen sulfide was added 5 h. Then, the mixture was placed at 0-5° C., and the solid precipitated, was filtered and provided the white solid (2.6 g), that was collected to obtain the target compound.

Elemental analysis: for C₉H₁₄Cl₂N₄OS, Cacld: C, 36.37%, H, 4.75%, Cl, 23.86%, N, 18.85%, S, 10.79%;

Found: C, 33.36%, H, 5.07%, Cl, 21.93%, N, 17.29%, S, 9.92%.

The water content in sample was 3.37%.

The content of reducing substance was 95.2% by iodometric titration. The structure is:

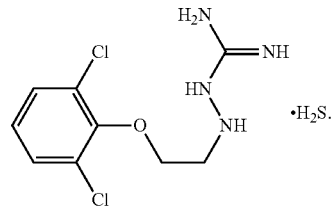 [SMILES: N=C(N)NNCCOc1c(Cl)cccc1Cl ; "·H2S."]

Example 17 1,8-diazabicycloundec-7-ene (DBU) hydrogen sulfide salt (C₉H₁₆N₂·H₂S, MW: 186.32)

DBU (30.4 g, 0.2 mol) was mixed with 100 mL water, and under the conditions that the temperature was kept at 25° C., 100 ml aqueous solution of 6.8 g hydrogen sulfide was added and mixed. Then, the mixed solution was rotatory evaporated at 50° C. and provided the solid (39 g), that was collected to obtain the target compound.

Elemental analysis: for C₉H₁₈N₂S, Cacld: C, 58.02%, H, 9.74%, N, 15.04%, S, 17.21%;

Found: C, 29.11%, H, 11.67%, N, 7.51%, S, 8.56%.

The water content in sample was 18.33%.

The content of reducing substance was 62.6% by iodometric titration. The structure is:

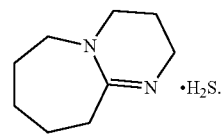

Example 18 4-Dimethylaminopyridine (DMAP) hydrogen sulfide salt ($C_7H_{10}N_2 \cdot H_2S$, MW: 156.25)

DMAP (24.4 g, 0.2 mol) was dissolved in 100 mL dichloromethane, and the solution was drop added to a three-necked bottle filled with hydrogen sulfide and reacted for 1.5 h. The color of reaction solution gradually became dark, and after stayed overnight, pale yellow solid precipitated, that was filtered and collected, to obtain the target compound (8.6 g).

Elemental analysis: for $C_7H_{12}N_2S$, Cacld: C, 53.81%, H, 7.74%, N, 17.93%, S, 20.52%;

Found: C, 43.82%, H, 8.68%, N, 14.61%, S, 16.72%.

The water content in sample was 5.62%.

The content of reducing substance was 85.9% by iodometric titration. The structure is:

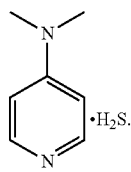

Example 19 Piperazidine Hydrogen Sulfide Salt ($C_4H_{10}N_2 \cdot H_2S$, MW: 120.22)

Piperazidine (17.2 g, 0.2 mol) was dissolved in 100 ml absolute ethanol, to which was added dry hydrogen sulfide at room temperature, and white needle solid precipitated at once. The mixture was stirred 5 min, filtered, and collected, to obtain the target compound (2.9 g).

Elemental analysis: for $C_4H_{12}N_2S$, Cacld: C, 39.96%, H, 10.06%, N, 23.30%, S, 26.67%;

Found: C, 36.02%, H, 8.68%, N, 20.91%, S, 23.92%.

The water content in sample was 2.98%.

The content of reducing substance was 92.9% by iodometric titration. The structure is:

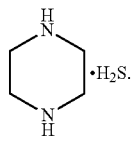

Example 20 Tryptamine Hydrogen Sulfide Salt ($C_{10}H_{12}N_2 \cdot H_2S$, MW: 194.30)

Tryptamine (3.2 g, 0.02 mol) was dissolved in 30 ml absolute ethanol, to which was added dry hydrogen sulfide, and white solid precipitated at once. The mixture was stirred 30 min, filtered, and collected, to obtain the target compound (0.8 g).

$^1$H NMR (400 MHz, $D_2O$): δ 2.96 (t, J=9.0 Hz, 2H), 3.11 (t, J=8.8 Hz, 2H), 7.03 (t, J=4.0 Hz, 1H), 7.08-7.13 (m, 2H), 7.34 (d, J=4.0 Hz, 1H), 7.49 (d, J=4.0 Hz, 1H);

$^{13}$C NMR (100 MHz, $D_2O$): δ 22.93, 40.10, 109.39, 112.35, 118.58, 119.71, 122.48, 124.53, 126.75, 136.71;

Elemental analysis: for $C_{10}H_{14}N_2S$, Cacld: C, 61.82%, H, 7.26%, N, 14.42%, S, 16.50%;

Found: C, 55.82%, H, 8.12%, N, 13.02%, S, 15.02%.

The water content in sample was 3.65%.

The content of reducing substance was 93.7% by iodometric titration. The structure is:

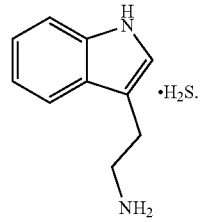

INDUSTRIAL APPLICABILITY

The present invention provides one new structural form of hydrogen sulfide ($H_2S$) donor that may have research and/or medicinal developmental values, i.e. hydrogen sulfide donor in organic salt form, and further provides the preparative method thereof. The structure of hydrogen sulfide donor according to the present invention is simple, and the preparative method thereof is also simple and feasible. Moreover, according to the requirement of research and development, various types of hydrogen sulfide donors can be obtained. After the hydrogen sulfide donor enters an organism, the in vivo dissociation and supply process of hydrogen sulfide is simple, rapid, and effective, and there is no requirement for enzyme or any other complicated conditions, thus the hydrogen sulfide donor has a great application prospect and value.

The invention claimed is:

1. A hydrogen sulfide donor in organic salt form, comprising a compound containing a guanidino group and hydrogen sulfide.

2. The hydrogen sulfide donor in organic salt form according to claim 1, wherein the compound is metformin.

3. The hydrogen sulfide donor in organic salt form according to claim 1, wherein the compound is guanethidine.

4. The hydrogen sulfide donor in organic salt form according to claim 1, wherein the compound is arginine.

5. A preparative method for hydrogen sulfide donor in organic salt form according to claim 1, comprising: mixing the compound containing a guanidino group and hydrogen sulfide in a solvent to form a reaction mixture; and separating the solvent from the reaction mixture to obtain the hydrogen sulfide donor in organic salt.

6. The preparative method for hydrogen sulfide donor in organic salt form according to claim 5, wherein the compound is in a free base form.

7. The preparative method for hydrogen sulfide donor in organic salt form according to claim 5, wherein the solvent is water or alcohol.

* * * * *